United States Patent [19]

Stypulkowski

[11] Patent Number: 5,037,497
[45] Date of Patent: Aug. 6, 1991

[54] METHOD OF FABRICATING AN ARRAY OF RECESSED RADIALLY ORIENTED BIPOLAR ELECTRODES

[75] Inventor: Paul H. Stypulkowski, North Oaks, Minn.

[73] Assignee: Cochlear Corporation, Englewood, Colo.

[21] Appl. No.: 555,242

[22] Filed: Jul. 19, 1990

Related U.S. Application Data

[62] Division of Ser. No. 238,553, Aug. 30, 1988, Pat. No. 4,961,434.

[51] Int. Cl.$^5$ .......................... B29C 45/14; B32B 1/10
[52] U.S. Cl. ................................... 156/245; 264/511;
264/154; 264/272.15; 264/277
[58] Field of Search .................. 264/511, 277, 272.15,
264/154; 156/245

[56] References Cited

U.S. PATENT DOCUMENTS

| | | | |
|---|---|---|---|
| 3,866,615 | 2/1975 | Hewson | 128/419 D |
| 3,916,513 | 11/1975 | Ballard | 264/277 |
| 4,284,856 | 8/1981 | Hochmair et al. | 179/107 E |
| 4,430,999 | 2/1984 | Brighton et al. | 128/419 F |
| 4,795,602 | 1/1989 | Pretchel et al. | 264/272.15 |
| 4,800,898 | 1/1989 | Hess et al. | 128/785 |

FOREIGN PATENT DOCUMENTS 1115352 12/1981 Canada .................................. 326/17
0183605 6/1986 European Pat. Off. .

OTHER PUBLICATIONS

Hochmair-Desoyer et al., Design and Fabrication of Multi-Wire Scala Tympani Electrodes, Annals of the New York Academy of Sciences, vol. 405, pp. 173-182.
Loeb et al., Design and Fabrication of an Experimental Cochlear Prosthesis, Medical & Biological Engineering and Computing, vol. 21, pp. 241-254 (May 1983).
Clark et al., A Cochlear Implant Round Window Electrode Array, The Journal of Laryngology and Otology, vol. 93, pp. 107-109 (Feb. 1979).
van den Honert et al., Single Fiber Mapping of Spatial Excitation Patterns in the Electrically Stimulated Auditory Nerve, Hearing Research, vol. 29, pp. 195-206 (1987).
Rubenstein et al., Recessed and Surface-Mounted Electrodes for Auditory Prostheses: Effects on Histopathology, Abstracts of the Tenth Midwinter Research Meeting, Association for Research in Otolaryngology (Feb. 1-15, 1987), p. 51.

Primary Examiner—Jan H. Silbaugh
Assistant Examiner—Angela Ortiz
Attorney, Agent, or Firm—Gottlieb, Rackman & Reisman

[57] ABSTRACT

An array of electrodes, suitable for use as an auditory prosthesis, and a method for fabricating such an array, are disclosed. The array includes an electrode body formed from an electrically insulating flexible material, preferably at least one annulus of an electrically insulating flexible material which is formed separately from the body and adhered thereto, at least one electrode positioned concentrically about each of the at least one annulus or electrode body, with the surface of each electrode being recessed and being exposed.

22 Claims, 2 Drawing Sheets

METHOD OF FABRICATING AN ARRAY OF RECESSED RADIALLY ORIENTED BIPOLAR ELECTRODES

This is a division of application Ser. No. 238,553 filed Aug. 30, 1988, now U.S. Pat. No. 4,961,434.

TECHNICAL FIELD

This invention relates to an array of electrodes, particularly to an auditory prosthesis having an array of radially oriented bipolar pairs of electrodes.

BACKGROUND OF THE INVENTION

Electrical stimulation of auditory nerve fibers in persons with total sensory deafness has been found to produce auditory sensations which can be perceived with sufficient familiarity, that with minimal training such sensations can be used for speech reception without additional cues. Electrical stimulation of the auditory nerve fibers in deaf patients is accomplished in a number of methods. Many methods of stimulating the auditory nerve fibers utilize an array of electrodes mounted in a flexible worm-like carrier which is inserted into the cochlea of a patient's ear.

Because the human cochlea has a snail-like configuration, two basic mechanical designs have existed for intracochlear electrodes. The first design has a shape which matches the coiled structure of the human cochlea. A prosthesis of this design is temporarily straightened before insertion and regains its coiled shape upon insertion in the cochlea. The second design is a straight prosthesis which is very flexible, but which has sufficient stiffness to be guided into the cochlea in the desired coiled shape. The straight flexible configuration is often preferred. See Hochmair-Desoyer et al., *Design and Fabrication of Multi-Wire Scala Tympani Electrodes*, Vol. 405, Annals of the New York Academy of Sciences, pp. 173-182.

The straight flexible auditory prosthesis will typically have an array of electrodes positioned in one of a number of various configurations along the length of the prosthesis. These various configurations include monopolar and bipolar pairs of electrodes, which pairs may be positioned either radially or longitudinally along the flexible prosthesis. See Loeb et al., Design and Fabrication of an Experimental Cochlear Prosthesis, *Medical & Biological Engineering and Computing*, May 1983, Vol. 21, pp. 241-254; Clark et al., A Cochlear Implant Round Window Electrode Array, *The Journal of Laryngology and Otology*, Feb. 1979, Vol. 93, pp. 107-109.

An auditory prosthesis having a radial bipolar configuration appears to be the most favorable electrode geometry for the multiple electrode array. See, van den Honert et al., Single Fiber Mapping of Spacial Excitation Patterns in the Electrically Stimulated Auditory Nerve, *Hearing Research*, 29 (1987) pp. 195-206.

In addition to having a radial bipolar configuration, it is desirable that the array of electrodes have a large surface area with individual electrodes having a surface area of greater than 0.25 mm$^2$. Further, the electrodes should have a decreased mass and volume so as to provide the desired mechanical characteristics to the prosthesis. The flexible prosthesis should also be capable of being easily fabricated.

Previous constructions have included so-called flame balls which are made by melting the ends of platinum or platinum iridium wires. Known practical flame ball constructions have longitudinal configurations as the volume of the flame balls does not permit radially placed electrodes. Another known configuration is that of electrode rings, which again are longitudinally spaced apart. Other known configurations include a mushroom shaped electrode having an outer domed surface approximating the surface of a flame ball protruding above the surface of the electrode body and with an inner stem anchoring the outer surface to the array. It is very difficult to place these electrodes radially, and, further, the large internal volume of the electrodes necessary to anchor them is undesirable.

SUMMARY OF THE INVENTION

Therefore, there is a need for an array of electrodes used, for example, as a flexible auditory prosthesis, which is easy to fabricate, which has recessed electrodes with little internal volume, providing a surface of the prosthesis which is very smooth, consisting of an electrically insulating flexible material. In addition, there is a need for such an array having a plurality of radially positioned electrodes.

The invention provides an electrode array suitable for use, for example, as an auditory prosthesis, the electrode array comprising an electrode body formed from an electrically insulating flexible material, at least one electrode, preferably a pair of electrodes, positioned concentrically about the electrode body, the outer surface of each electrode being recessed and exposed. Preferably the electrodes are positioned on said electrode body through an electrically insulating, flexible annulus, preferably annuli, formed separately from the electrode body and adhered thereto.

The electrodes are preferably made from a metal foil having a convex contact surface and a concave underside. The body and the annuli are preferably made from an elastomeric material. The body preferably has a cylindrical or tapered cylinder configuration.

The invention also provides a method for fabricating an electrode array suitable for use, for example, as an auditory prosthesis, comprising the steps of (a) providing an injection molding mold having a molding cavity and at least one vacuum hole through the wall of one half of the mold; (b) providing an electrode for each vacuum hole, preferably formed from an electrically conductive foil and having a convex contact surface; (c) forming an annulus of an electrically insulating flexible material about each vacuum hole to create a contact well around each of the holes; (d) positioning an electrode over each of the wells; (e) applying a vacuum to each of the vacuum holes to hold the electrodes in place over the wells; (f) fastening the mold halves together and molding the body of the electrode array structure from an electrically insulating flexible material, whereby the annuli and the electrodes are adhered to the body; and (g) removing the electrode array from the mold whereby an electrode array with at least one electrode is provided.

The invention also includes forming the contact wells of step (c) by providing a layer or sheet of electrically insulating material along the walls of the molding cavity and forming a contact well around each vacuum hole.

DETAILED DESCRIPTION

Figure 1:
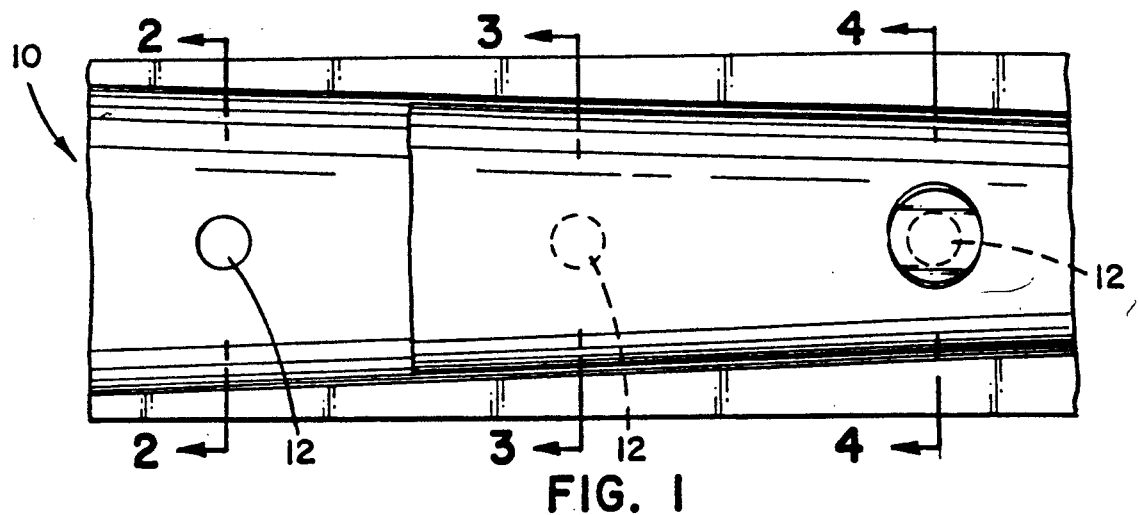
FIG. 1 is a top view of one-half of a mold used in a method of the present invention showing three steps of the method.

Referring to FIG. 1, a portion of one half of a two part mold used to make an electrode array or assembly of one embodiment of the present invention is shown. In practice, the preferred embodiment would contain, for example, ten pairs of radially positioned electrodes, and therefore, a mold such as shown in FIG. 1 would have ten holes in each side of the mold.

In FIG. 1 there is a mold 10 having a plurality of vacuum holes 12 and a molding cavity 14 which is tapered towards one end of the mold. The three holes 12, shown in FIG. 1, each represent a different step in the method for fabrication of a flexible electrode array of the invention.

Figure 2:
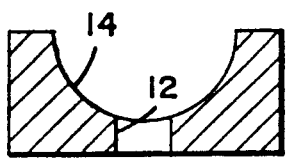
FIG. 2 is a cross-section along line 2—2 of FIG. 1.

FIG. 2 depicts a cross-section of the cylindrical or tapered cylinder molding cavity 14 and a vacuum hole 12 prior to any step of the method of the invention.

Figure 3:
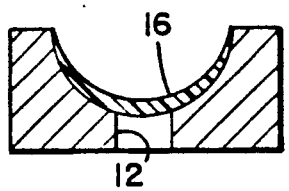
FIG. 3 is a cross-section along line 3—3 of FIG. 1 showing a layer of flexible material placed in the mold around a vacuum hole.

Referring to FIG. 3, a layer of an electrically insulating flexible material 16 is placed around the vacuum hole 12 along the walls of the molding cavity 14. The flexible material 16 may be thinned with a suitable solvent and then placed in the molding cavity 14. When the solvent evaporates, the thin flexible sheet 16 remains.

Figure 4:
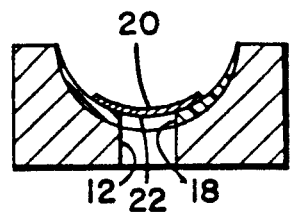
FIG. 4 is a cross-section along line 4—4 of FIG. 1 showing an electrode being inserted over a contact well formed in the layer of flexible material.

Referring to FIG. 4, a contact well 18 is formed in the thin flexible sheet 16. The contact well 18 is in alignment with the vacuum hole 12. A vacuum is drawn through the hole 12 and well 18 and an electrode 20 is positioned above the well 18 and held in place by vacuum. The electrode 20 has a concave surface 21 and a convex contact surface 22. Contact wires 23 are joined, preferably by welding, to the concave surface 21 of the electrode 20. The contact surface 22 is then positioned with the surface 22 facing toward the well 18.

Figure 5:
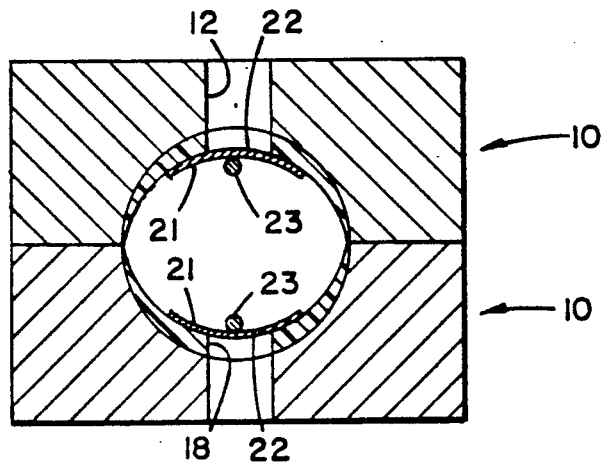
FIG. 5 is a cross-section of two halves of the mold showing the contact wires.
Figure 6:
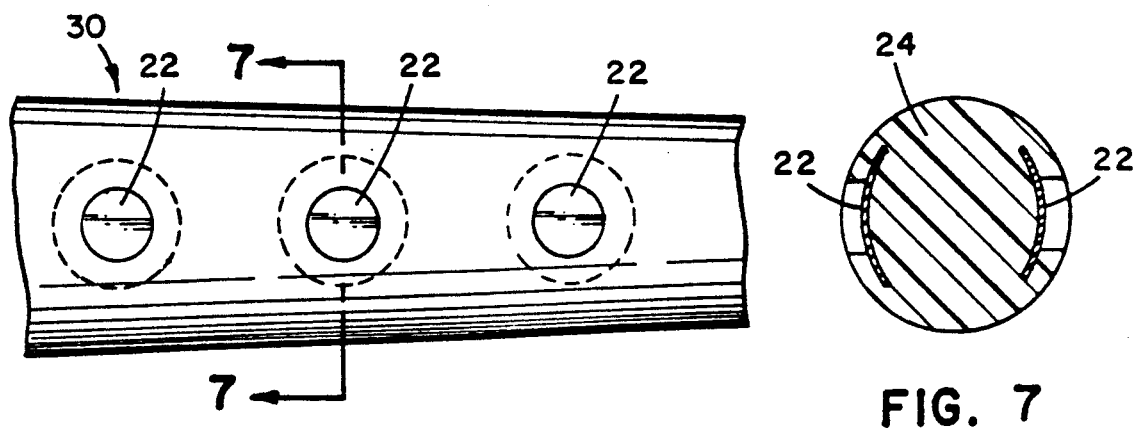
FIG. 6 is a partial perspective view of an electrode array of the present invention.
Figure 7:
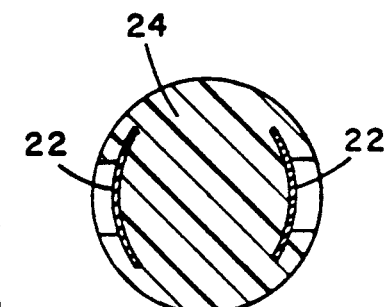
FIG. 7 is a cross-section along 7—7 of FIG. 6.

Referring to FIGS. 5 and 7, the two molds 10 having the flexible sheet 16 and electrode 20 positioned within the opposing sides of the mold cavities 14 are shown. The body 24 is injection molded with the same or another flexible electrically insulating material and the sheet 16 and the electrode 20 are adhered to the body 24 as best shown in FIG. 7. The finished electrode array or assembly 30, FIGS. 6 and 7, is removed from the mold 10 and an electrode array 30 having radially placed contacts is provided.

Figure 8:
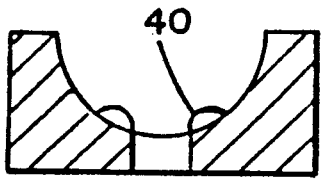
FIG. 8 is a cross-section similar to FIG. 3, showing the preferred embodiment of the invention
Figure 9:
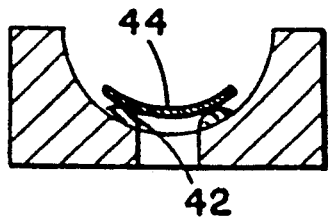
FIG. 9 is a cross-section similar to FIG. 4, showing the preferred embodiment of the invention.

Referring now to FIGS. 8 and 9, cross-sections similar to FIGS. 3 and 4 of a preferred embodiment of the invention are shown. In FIG. 8 an annulus 40 formed from an electrically insulating flexible material is provided around the vacuum hole 12 along the walls of the molding cavity 14. The annulus 40 includes a contact well 42. In FIG. 9 an electrode 44 is postioned concentrically with the annulus 40.

Figure 10:
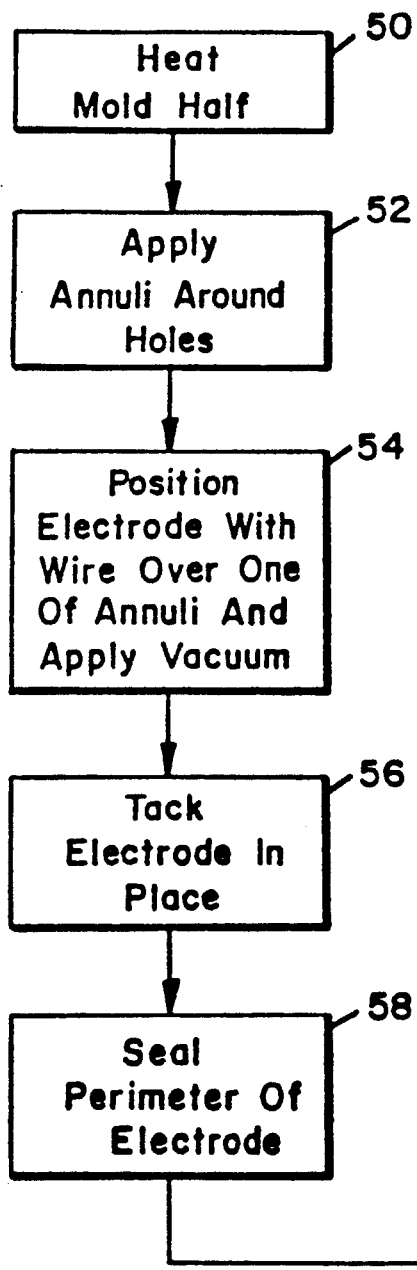
FIG. 10 is a flow chart of a preferred method of the present invention.
Figure 10:
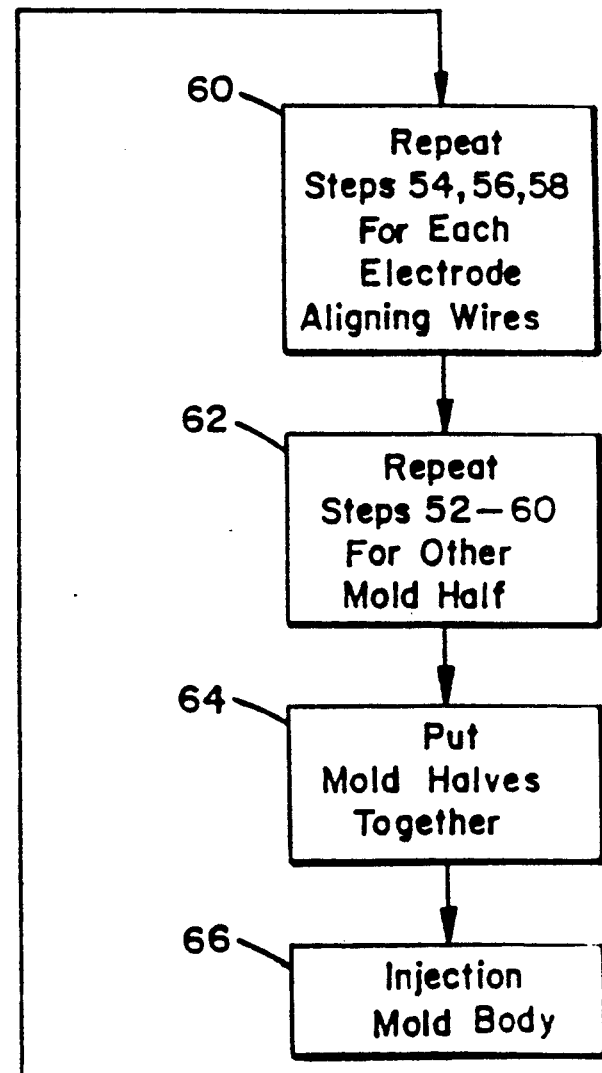

Referring now to FIG. 10, a preferred method of the present invention is described. A mold as described above having two halves is provided and one-half of the mold is heated (50). Next, an annulus is applied around each of the vacuum holes (52). An electrode with a contact wire attached is positioned over one of the annuli and a vacuum is applied through the vacuum holes (54). The electrode is tacked into place with an elastomeric material (56) and then the entire perimeter of the electrode is sealed with an elastomeric material (58). Next, steps 54, 56 and 58 are repeated for each electrode, aligning the contact wires longitudinally in the mold (60). Next, steps 52-60 are repeated for the second half of the mold. The two halves of the mold are then put together (62) and the body of the array of electrodes is injection molded (64).

COMPONENTS

The material which is used to form the annuli or the sheet and the material molded to make the body of the electrode, is a flexible electrically insulating material, which is preferably elastomeric. Because electrode arrays of this type can be used as an auditory prosthesis which is inserted into the ear, the flexible material is more preferably a medical grade elastomeric material.

It is preferred that the annuli or sheet and the electrode body be made from the same flexible material for simplicity in fabrication and to aid in adhesion between the two layers. Preferred medical grade elastomers which may be utilized in the invention are silicone rubbers of the Silastic ® (a registered trademark of Dow-Corning) series medical grade elastomers, commercially available from Dow-Corning Medical Products, Midland, MI. Silastic ® MDX-4-4210, medical grade elastomers, and Silastic ® 382, medical grade elastomers, are examples of suitable, electrically insulative, flexible, medical-grade elastomeric materials. These materials are essentially non-toxic, non-irritating, non-sensitizing and can be placed in contact with skin or other tissues without producing adverse effects. In addition, these elastomeric materials are dimensionally and thermally stable, resistant to oxidation and sunlight, and do not become hard with age.

The Silastic ® 382 medical grade elastomer is supplied as two separate liquids, namely, an opaque viscous elastomeric base and a catalyst. Silastic ® 382 medical grade elastomer is represented by Dow-Corning to be comprised of polydimethylsiloxane and silica filler. The catalyst is said to be a specially tested grade of stannousoctoate. When mixed together the Silastic ® 382 elastomer remains workable for approximately 10 minutes and vulcanization is complete is about 30 minutes. The working and vulcanization times may be varied by changing the amount of catalyst.

Silastic ® MDS-4-4210 medical grade elastomer is a clear to translucent high strength clean grade silicone rubber which cures at room temperature. Silastic ® MDS-4-4210 elastomer is made by mixing a curing agent with a base material in an approximate ratio of one part of curing agent to 10 parts by weight of the base material. Curing sufficient for handling of the material occurs in about 24 hours at 23° C., with full cure achieved in about three days at room temperature. Curing may be accelerated by increasing the temperature.

It is desirable that the flexible material have sufficient tensile strength to provide the desired flexibility to the finished prosthesis to allow for insertion into the cochlea. Other medical grade elastomeric materials having suitable flexibility and the other desired properties can also be used.

The electrodes used in the present invention are preferably formed from platinum or platinum-iridium foil having a thickness typically ranging from $1 \times 10^{-3}$ to $5 \times 10^{-3}$ cm. Circles or ovals typically having a maximum diameter of about 0.75 mm are punched from the foil, preferably at least a portion of the contact is formed into a convex shape, preferably approximating the shape of the mold. Other material having suitable flexibility, thinness, electrical conductivity and tissue compatibility may also be used.

In addition to the elastomeric material and the foil electrode material, the electrode arrays include contact wires. The contact wires are typically Teflon ® coated platinum or platinum-iridium wires having diameters typically ranging from $1 \times 10^{-3}$ to $1 \times 10^{-2}$ cm. These wires are welded to the individual electrodes typically on the inside or concave portion of the electrodes, as shown in FIG. 5.

FABRICATION

The electrode arrays of the invention may be fabricated by first spreading a thin layer of the flexible material, preferably a Silastic ® medical grade elastomer from Dow-Corning, on the inside of the mold cavity. The Silastic ® elastomer type material may be dissolved in a suitable solvent prior to coating on the inside of the molding cavity. Suitable solvents, such as xylene, thin the elastomeric material for uniform application. In addition, when the solvent evaporates, a suitable layer of the elastomeric material is provided in a concave configuration along the walls of the molding cavity (see FIG. 3). To achieve the desired thickness of the layer, the ratio of the solvent to elastomeric material can be varied to precisely determine the thickness of the resultant sheet.

It is preferable to provide an annulus of elastomeric material around the perimeter of the vacuum holes to provide contact wells. If instead of an annulus a sheet of flexible material is provided, contact wells must be formed in the sheet. The wells may simply be punched out with, for example, a sharpened hypodermic needle. Another way to produce the wells is by applying a vacuum to the mold before the elastomeric material is fully cured or set, thereby drawing the elastomeric material from the contact well out through the vacuum hole. Regardless of the method, it is desirable to produce a clean sharp hole (contact well) through the thin layer of elastomeric material.

Once the annulus of elastomeric material is in place, or the contact well is formed, the electrodes themselves are placed in position. As described above, these electrodes are preferably made from platinum or platinum-iridium foil. The electrodes are welded to the appropriate lead or contact wires, preferably made of a thin Teflon ® fluorinated polymer (registered trademark of Dupont) coated platinum-iridium wire. The contacts are placed over the contact wells and are held in place by means of vacuum pressure. Because the platinum foil is preferably relatively soft, the contacts can be further formed into place by gentle pressure.

It is preferred that the mold be heated before the annuli are positioned about the vacuum holes. Heating the mold provides a more flowable material to give a smooth surface to the annuli. The temperature of the mold is preferably set so the flexible material cures in one-three minutes. The temperature of the mode is typically set between 25° and 120° C., preferably about 80° C. to 100° C.

It may also be desirable to tack the electrodes into place with additional elastomeric material, which may also be thinned with solvent, as desired. The electrode may also be sealed into place by placing additional elastomeric material around the perimeter of the electrode. The elastomeric material is then allowed to cure or dry.

This process is repeated for each of the contacts in each of the pair of molds. Typically 1 to 10 electrodes are provided in each half of the mold for a total of 1 to 10 pairs of preferably radially placed electrodes.

The dimensions of the array of electrodes is dictated by its intended use. The electrodes themselves should be dimensioned and positioned so as to not contact or short-out a neighboring electrode. An array of electrodes used as an auditory prosthesis in a human cochlea would be dimensioned to fit into the human cochlea which has an average length (unwound) of about 32 mm. The average length of an auditory prosthesis array typically may range from 15 to 25 mm. The array is an elongate body having a radial cross-section which is preferably circular or oval to fit snuggly in the cochlea. The individual electrodes may be spaced from almost touching to 15 to 25 mm apart, typically with about 1-2 mm center-to-center spacing. The auditory prosthesis is tapered with the narrow end inserted first. The narrow or tip diameter may typically range from about 0.2 mm to 0.8 mm with the wide end ranging from about 1 to 2 mm, with 1.0 to 1.4 being preferred. The vacuum holes on the mold used to make an auditory prosthesis are typically on the order of 0.3 to 0.5 mm. The size of the annulus would typically be 0.5 mm diameter round to about 0.5 to 0.75 mm eliptical.

The thickness of the annuli or sheet of flexible material determining the depth the electrode is recessed from the surface of the electrode array is about 10% to less than 50% of the minimum diameter of the electrode body, and preferably about 25%. For example, if the tip of the prosthesis has a diameter of 0.5 mm the electrodes are preferably recessed about 0.125 mm throughout the length of the prosthesis.

The two mold halves are then fastened together so that the electrodes form pairs of preferably diametrically opposed, radially spaced electrodes. The body of the electrode array is molded from an electrically insulative flexible material, preferably an elastomeric material, typically the same material which was used to form the annuli or sheet on the perimeter of the mold. The body is then preferably injection molded, preferably at room temperature.

The cure of the flexible material can be hastened by placing the mold in an oven after molding at an elevated temperature for a desired period of time. The electrode is removed from the mold by carefully removing one half the mold at a time and trimming any excess flexible material away from the edges of the electrode with a sharpened device. Also, any flexible material which is covering the contact surface is carefully removed.

The electrical properties of the electrode are then tested.

What is claimed is:

1. A method for fabricating an electrode assembly in a body of electrically insulating flexible material comprising the steps of:

(a) providing a two-part injection molding mold having a molding cavity and at least one vacuum hole through a wall in at least one of the parts of the mold;

(b) providing an electrode for each vacuum hole;

(c) forming an electrically insulating flexible material about each vacuum hole to create a contact well around each said hole;

(d) positioning an electrode over each said contact well;

(e) applying a vacuum to each vacuum hole to hold the electrode in place over the contact well;

(f) fastening the mold parts together and molding the body of the electrode assembly in the mold from an electrically insulating flexible material whereby each said electrode is adhered to the body; and (g) removing the electrode assembly from the mold whereby an electrode assembly with at least one electrode is provided.

2. The method according to claim 1 wherein the mold parts when fastened together form a generally conical chamber having a central longitudinal axis, and wherein each said vacuum hole is positioned so that when the mold parts are fastened together each said hole is positioned radially relative to said axis.

3. The method according to claim 1 wherein each said electrode has a convex surface thereon.

4. The method according to claim 1 wherein said electrically insulating flexible material and said body are formed from an elastomeric material.

5. The method according to claim 2 wherein each of the mold parts includes at least one vacuum hole through a wall thereof and is processed in accordance with steps (b)–(e), and wherein each said vacuum hole is positioned so that when the mold parts are fastened together the holes are diametrically opposed to one another.

6. The method according to claim 1 further wherein step (f) is accomplished by tacking each of the electrodes in place with a flexible material.

7. The method according to claim 6 wherein each said electrode includes a perimeter, and wherein the perimeter of each said electrode is sealed with a flexible material.

8. The method according to claim 1 wherein step (c) is accomplished by coating the wall of each part of the mold with a sheet of electrically insulative flexible material and forming contact wells therein.

9. The method according to claim 8 further wherein step (c) is accomplished by applying a solvent thinned elastomeric material to the walls wherein the solvent evaporates to leave a sheet of elastomeric material coated on the walls.

10. The method according to claim 8 wherein the contact wells provided in step (c) are cut from the sheet with a punch.

11. The method according to claim 8 wherein the contact well provided in step (c) is formed by applying a vacuum to the mold to draw flexible sheet material out through said vacuum hole.

12. The method according to claim 1 wherein the electrode comprises a foil selected from a group containing platinum and platinum-iridium.

13. The method according to claim 1 wherein the molding cavity has a circular cross-section.

14. The method according to claim 1 wherein the body is injection molded.

15. The method of claim 1 wherein the flexible material is a medical grade silicone rubber.

16. The method according to claim 1 wherein positioning of step (e) includes further forming each electrode into place with gentle pressure.

17. The method according to claim 1 wherein each electrode provided in step (b) has a lead wire attached thereto and further wherein in step (d) the lead wires are positioned radially inward of the electrode during the molding of step (f) whereby the possibility of extruding lead wires is eliminated.

18. The method according to claim 1 wherein the mold is heated to about 25° C.–120° C. prior to step (c).

19. A method for imbedding an electrode in an electrode assembly body comprising the steps of:

(a) providing a mold having a wall which defines a molding cavity therein and having at least one vacuum hole passing through the wall into the molding cavity;

(b) providing an electrode;

(c) coating the wall of the mold surrounding each vacuum hole with an annulus of flexible material to form a contact well;

(d) positioning an electrode over the well;

(e) applying a vacuum to the vacuum hole to hold the electrode in place over the contact well and tacking the electrode in place;

(f) molding the body of the electrode assembly with flexible material in the mold so that the annulus and electrode are adhered to the body; and (g) removing the electrode assembly and body from the mold.

20. The method according to claim 19 wherein said flexible material is an elastomeric material.

21. The method according to claim 19 wherein the molding cavity has a curved cross-section, and wherein the electrode provided in step (b) is stamped out of a foil selected from a group containing platinum and platinum-iridium and is preformed in an electrode form mold having a curvature similar to the curvature of the molding cavity.

22. The method according to claim 19 wherein the electrode provided in step (b) has a lead wire attached thereto and further wherein in step (d) the lead wire is positioned radially inward of the annulus during the molding of step (f) whereby the possibility of an extruding lead wire is eliminated.

* * * * *